US008702687B2

(12) United States Patent
Tilleman

(10) Patent No.: US 8,702,687 B2
(45) Date of Patent: Apr. 22, 2014

(54) SURGICAL LASER SYSTEMS FOR SOFT AND HARD TISSUE AND METHODS OF USE THEREOF

(75) Inventor: Michael M. Tilleman, Arlington, MA (US)

(73) Assignee: Luxon, Inc., Arlington, MA (US)

( * ) Notice: Subject to any disclaimer, the term of this patent is extended or adjusted under 35 U.S.C. 154(b) by 2166 days.

(21) Appl. No.: 11/529,072

(22) Filed: Sep. 28, 2006

(65) Prior Publication Data

US 2007/0100330 A1    May 3, 2007

Related U.S. Application Data

(60) Provisional application No. 60/732,801, filed on Nov. 3, 2005.

(51) Int. Cl.
*A61B 18/20* (2006.01)

(52) U.S. Cl.
USPC .......................... 606/6; 606/3; 606/4; 606/10

(58) Field of Classification Search
USPC ........................................... 606/41–52, 2–19
See application file for complete search history.

(56) References Cited

U.S. PATENT DOCUMENTS

| | | | |
|---|---|---|---|
| 3,633,126 A | 1/1972 | Martin et al. | |
| 4,872,177 A | 10/1989 | Baer et al. | |
| 4,901,330 A | 2/1990 | Wolfram et al. | |
| 4,951,663 A | 8/1990 | L'Esperance, Jr. | 128/395 |
| 5,066,291 A | 11/1991 | Stewart | 606/3 |
| 5,125,922 A | 6/1992 | Dwyer et al. | 606/3 |
| 5,139,494 A | 8/1992 | Freiberg | 606/3 |
| RE34,192 E | 3/1993 | Baer | |
| 5,257,935 A | 11/1993 | Vassiliadis et al. | |
| 5,304,167 A | 4/1994 | Freiberg | |
| 5,423,798 A * | 6/1995 | Crow | 606/4 |
| 5,623,510 A | 4/1997 | Hamilton et al. | |
| 5,841,805 A | 11/1998 | Injeyan et al. | |
| 6,090,102 A | 7/2000 | Telfair et al. | |
| 6,167,069 A | 12/2000 | Page et al. | |
| 6,341,139 B1 | 1/2002 | Ohtsuka et al. | |
| 6,458,120 B1 | 10/2002 | Shen et al. | |
| 6,569,156 B1 | 5/2003 | Tankovich et al. | 606/10 |
| 6,650,663 B1 | 11/2003 | Diening et al. | |
| 6,998,567 B2 | 2/2006 | Yeik | |

FOREIGN PATENT DOCUMENTS

EP    0198959    10/1986    ............. A61B 17/36

OTHER PUBLICATIONS

U.S. Appl. No. 60/732,801, "Surgical Laser for Soft and Hard Tissue Operating on Two Wavelengths," filed Nov. 3, 2005.
International Search Report for PCT/US06/60429 filed Nov. 1, 2006. Applicant: Luxon, Inc. et al. Title: Surgical Laser Systems for Soft and Hard Tissue and Methods of Use Thereof.

* cited by examiner

*Primary Examiner* — Aaron Roane
(74) *Attorney, Agent, or Firm* — Burns & Levinson LLP; Orlando Lopez

(57) ABSTRACT

Laser systems operating at two or more wavelengths.

28 Claims, 11 Drawing Sheets

SURGICAL LASER SYSTEMS FOR SOFT AND HARD TISSUE AND METHODS OF USE THEREOF

CROSS REFERENCE TO RELATED APPLICATIONS

This application claims priority of U.S. Provisional Application 60/732,801, "Surgical Laser for Soft and Hard Tissue Operating on Two Wavelengths," filed on Nov. 3, 2005, which is incorporated by reference herein.

BACKGROUND

These teachings relate generally to lasers, and, more particularly, to laser systems operating at two or more wavelengths.

Traditional laser tools for cutting biological soft tissue comprise lasers radiating around 1 microns, including laser diodes based on InGaAs semiconductor. At the same time, traditional laser tools for ablating biological hard tissue comprise lasers radiating in the wavelength range of 2.5-3 microns or around 10 microns. In many instances the surgeon, medical practitioner or dentist requires the application of both laser types for a smooth and easy transition between various tissues and convenience for the patient.

Previous laser tools have generally been separated into applications for the soft and hard tissue. A laser apparatus for removing only dental enamel and dentin, pumped by unspecified means, has been previously disclosed. The practical application of a laser at 2.5-3 microns requires the use of specialized fibers, for instance Germanium-oxide or Fluorozirconate or fluoride glass fibers, for the purpose of beam delivery to the target. Diode pumped laser of this category have been previously disclosed. An efficient delivery of 2.5-3 microns radiation in each of the above disclosures over distances of a meter or a few meters can be accomplished only by employing such specialized fibers as aforementioned that have the characteristics of brittleness, water solubility, toxicity, sensitivity to UV exposure, limited mechanical strength, low temperature damage threshold and low laser damage threshold.

The capability of emitting and delivering two laser wavelengths, one that of the diode pump and the other at 2.94 microns, has been previously disclosed for an ophthalmic surgical laser featuring parameters specifically applicable to that use.

Regarding lasing media of interest, a laser gain medium comprising undoped and doped host materials bonded to one another has been previously disclosed wherein the doping is by laser active rare-earth ions so that thermal lensing in reduced.

A solid-state laser placed in a hand-held surgical probe connected to the pump laser diode by a fiber bundle has been previously disclosed where the laser is limited to low energy per pulse ~<10 mJ, low pulse repetition rate ~20 Hz. This limits the practical use of that device to ophthalmic applications and not for hard tissue ablation.

Also regarding gain media, thin slab laser crystals in which the laser beam propagates at a shallow, grazing angle relative to one of the slab long sides have been previously described. A composite slab where the doped, sub-millimeter laser active crystal is diffusion bonded to an undoped cap made of the same host material has also been previously described. Previous disclosures are related to Nd based lasers.

There is therefore a need for a handheld surgical laser system which is suited to cut soft biological tissues and ablate hard biological tissues.

BRIEF SUMMARY

In one embodiment, the system of these teachings includes an electromagnetic radiation source capable of emitting electromagnetic radiation in at least a first range of wavelengths, the at least the first range of wavelengths being selected to enable surgical operation on soft tissue, and a first reconfigurable redirecting optical component capable of being placed into one of at least two configurations, the first reconfigurable redirecting optical component being disposed to receive electromagnetic radiation from the electromagnetic radiation source. One of the at least two configurations corresponds to allowing propagation, without redirection, of at least a portion of the electromagnetic radiation in the at least the first range of wavelengths. A direction of propagation, without redirection, of the at least a portion of the electromagnetic radiation in the first range of wavelengths constitutes an output direction.

In that embodiment, the system also includes an optical resonator component comprising two reflecting end pieces, one of the two reflecting end pieces being partially reflecting and a gain medium disposed between the two reflecting end pieces. Another one of the at least two configurations of the first reconfigurable redirecting optical component corresponds to redirecting propagation of at least another portion of the electromagnetic radiation in the at least first range of wavelengths. The optical resonator and the gain medium are disposed such that the gain medium receives the at least another portion of the electromagnetic radiation in the at least the first range of wavelengths after being redirected.

The gain medium is capable of being pumped by the at least another portion of the electromagnetic radiation in the at least the first range of wavelengths after being redirected and capable of, after being pumped, emitting electromagnetic radiation in a second range of wavelengths. The second range of wavelengths is selected to enable surgical operation on hard tissue. A pumping power of the electromagnetic radiation in the at least the first range of wavelengths being selected to enable a power of emitted electromagnetic radiation in the second range of wavelengths sufficient for surgical operation on hard tissue.

In that embodiment, the system also includes a second reconfigurable redirecting optical component capable of being placed into one of at least two configurations. One of the at least two configurations of the second reconfigurable redirecting optical component corresponds to redirecting emitted electromagnetic radiation in the second range of wavelengths, the redirecting enabling propagation of the emitted electromagnetic radiation in the second range of wavelengths substantially along the output direction. Another one of the at least two configurations of the second reconfigurable redirecting optical component allows propagation, without redirection, of the at least a portion of the electromagnetic radiation in the at least the first range of wavelengths. The system also includes a selecting component capable of selecting a configuration of the first reconfigurable redirecting optical component and the second reconfigurable redirecting optical component.

Other embodiments in which the electromagnetic radiation source is capable of emitting electromagnetic radiation in a first and a third range of wavelengths are also disclosed.

In another embodiment, the system of these teachings includes a housing capable of being handheld, a number of the components being disposed in the housing.

Method for using the system of these teachings are also disclosed.

For a better understanding of the present invention, together with other and further needs thereof, reference is made to the accompanying drawings and detailed description and its scope will be pointed out in the appended claims.

DETAILED DESCRIPTION

Figure 1:
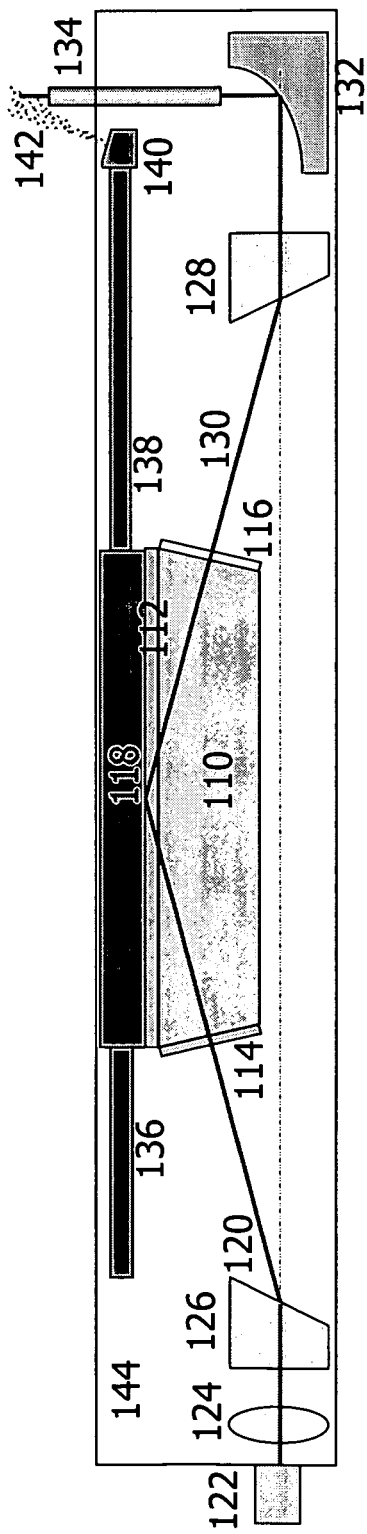
FIG. 1 is a schematic representation of an embodiment of the system of these teachings.

In one embodiment, the present teachings include a laser system operating on two or three wavelengths by specifically selecting the desired wavelength, where the first wavelength in the range of about 750 nm to about 1100 nm acts as a surgical tool for soft tissue such as skin, muscles, tendons, fibrous tissues, fat, blood vessels, nerves, synovial tissues or any tissues that do not contain minerals (such as bone), another wavelength in the range of about 1450 nm to about 1600 nm acts as a surgical tool for soft tissue located in depth such as muscles, tendons, fibrous tissues, fat, blood vessels and yet another wavelength in the range of about 2500 nm to about 3500 nm acts as an ablation, excavation and cutting tool for a hard tissue, such as bone, enamel, dentine, cartilage and urinary stones. Any laser beam in these three wavelength ranges or their combination can be emitted by user selection, by pushing a knob on the handpiece or pressing a key on the control console or changing handpieces and so on.

In one embodiment, the laser system includes three elements: pump laser, which in one embodiment, but not limited to, is a laser diode emitting power or energy in either of the two wavelength ranges of 750 nm-1100 nm (in one embodiment, but not limited to, an InGaAs or InAlGaAs semiconductor laser) or 1450 nm-1600 nm (in one embodiment, but not limited to, an InP or InGaAsP semiconductor laser) which overlap absorption spectral lines of the (in one embodiment, but not limited to, erbium trivalent ion gain medium) gain medium, an optical fiber (in one embodiment, but not limited to, made of silica) which delivers the laser diode beam to a handpiece, and a handpiece containing the laser generating a beam at 2500 nm-3500 nm, referred to as diode-pumped-solid-state (DPSS) laser. In one embodiment, the pump laser emits relatively high average power in the range between 1 W and 1 kW, efficiently coupled to the optical fiber which couples efficiently pump beam to the handpiece. (Although the laser generating a beam at 2500 nm-3500 nm is referred to as a DPSS, it should be noted that other embodiments of the pump laser, such as, but not limited to, a fiber laser of appropriate wavelength, are possible.)

In one embodiment, the laser emitting the wavelength in the range of 2500 nm to 3500 nm is configured inside a handpiece, so as to permit the emission of the first or the second or the third laser wavelength or their combination, as pre-selected by the user. This handpiece contains the DPSS laser, and it also may contain the mechanism to select the emission to the target of any of the laser wavelengths. On exiting the delivery fiber the pump laser is directed to and focused on the DSPP laser gain medium, using one or a few optical components such as lenses, prisms and mirrors. In one embodiment, the gain medium of the DSPP laser includes an Erbium doped Yttrium Aluminum Garnet (Er:YAG), Erbium doped Yttrium-Scandium-Gadolinium Garnet (Er:YSGG), Erbium doped Yttrium Lithium Fluoride (Er:YLF) crystal or Erbium doped another crystalline or amorphous host, such as fluorinated glass, or other media capable of laser emission in the range of 2500 nm to 3500 nm. These host materials for the $Er^{+3}$ ions can also be co-doped by sensitizer materials such as Ytterbium or Praseodymium whose presence in the host enhances the population inversion of the Er ions. The gain medium of the DPSS laser is configured so as to efficiently convert the pump power and energy to that of the DPSS laser, generate minimal heat and emit pulses with precise time format. Both the maximum output power and minimum heating are accomplished by making a thin slab. (The term "slab", as used herein, includes a disk.) While the average output power scales inversely with the slab thickness, maximized contact area to a heat sink as well as good thermal contact between the gain medium and the heat sink removes efficiently the excess heat from the lasing area, thus reducing thermal lensing and improving the laser beam quality. In one embodiment, control of appropriate pulse format at good extraction efficiency is accomplished by a method known as gain switching.

In addition to operating in quasi-CW mode where pulse duration of the DPSS laser is determined by that of the pump laser, one of the embodiments of this teachings the DPSS laser is gain switched by the pump laser. In gain switching the pump power is increased rapidly so that the population inversion of the DPSS laser is well above the threshold value by the time its first pulse evolves. Then the photon flux drives the population inversion down below the threshold, thus consequently terminating the optical pulse. Gain switching is a substitute to Q-switching of laser media with relatively upper state short lifetime and ideal for laser systems with typical low gain factors, such as is the $Er^{+3}$ laser on the $^4I_{11/2}$-$^4I_{13/2}$ transition. Whereas in the quasi-CW mode of operation the laser pulses have a duration spanning the range of tens microseconds to milliseconds, the gain switching generates pulses that may be shorter than a nanosecond.

To perform ablation of hard tissue such as dentine or enamel the laser fluence at the wavelength around 3 microns must be above the threshold of about 4 $J/cm^2$. Such fluence can be, in one embodiment, obtained by focusing the laser, hence the importance of good beam quality. Higher fluence results in deeper ablation crater and faster material removal.

That trend holds up to fluence magnitudes around 40 J/cm$^2$, after which the improvement becomes marginally small.

Optical conversion efficiency of a diode-pumped solid-state laser may be as high as approximately the quantum defect, resulting in about 30% for the embodiment in which the pump laser at 976 nm pumps an Er:YAG laser that emits at the wavelength of 2.94 micron. In many embodiments, the conversion efficiency may be lower, say 15%-25%, depending on the pump intensity and pump absorption. For example, in one embodiment, for a pump having a power of 40 W focused to a spot size of about 600 microns, 8 W are produced by a laser at 2.94 micron having a beam aperture slightly less than 600 microns. Such a system determines a near field intensity of about 28 kW/cm$^2$. For a pulsed mode of operation pulsed with a typical (but not a limit of these teachings) pulse duration of 100 ms, the resulting near field fluence is 2.8 J/cm$^2$, which is short of the threshold for hard tissue ablation of 4 J/cm$^2$. The fluence can be magnified by focusing the laser beam to a smaller spot size. Focusing the laser beam to a smaller spot size can be, in one embodiment, accomplished by magnifying the laser aperture and a subsequent focusing of the beam. Considering, in one instance, a beam divergence of about 3 times the diffraction limit having been magnified to a spot size of about 1 mm and a focusing optical component with a focusing length of about 20 mm, a focal spot of about 224 micron is attained, resulting in the far field fluence of about 20 J/cm$^2$. A fluence of about 20 J/cm$^2$ is considered very effective in ablating hard tissue, for instance enamel and dentin.

In another embodiment the pump laser diode may radiate at the wavelength of 1500 nm, resulting in optical conversion efficiency to 2.94 microns of about 40%. Consequently, the aforementioned 2.94 microns laser power, intensity and fluence can be attained by using a pump power of 20 W.

In embodiments in which 976 nm radiation is used, by using the above described focusing technique, high intensity and fluence are obtained. In one instance, electromagnetic radiation from a laser diode propagating through an optical fiber with a core diameter of about 400 microns and numerical aperture of about 0.22, when collimated on outcoupling by a lens with a focal length of about 40 mm, the electromagnetic radiation emerges with a beam aperture of about 12 mm. In the embodiment in which the divergence of the pump laser-diode is about 50 times the diffraction limit, a focal spot of about 100 microns is obtained. For a power of about 10 W, this results in an intensity of about 120 kW/cm$^2$ and in a pulsed operation as described above, in a far field fluence of about 12 J/cm$^2$. A fluence of about 12 J/cm$^2$ is considered very effective in cutting soft tissue, for instance skin.

In applications including lithotropsy, the stones are ceramic like, therefore similar to hard tissue. The above considerations for hard tissue can also be applied to lithotropsy.

The laser in any of its emitting wavelengths or their combination is delivered from the handpiece to the target, in one embodiment, a soft or hard biological tissue, by the means of a waveguiding tip, in one embodiment, but not limited to, made of dry quartz or sapphire fiber. If a dry quartz tip is used, it may be configured as an optical fiber comprising core and cladding thus guiding the laser beam without phase degradation. Both sapphire and dry quartz bulks having a thickness of 10 mm transmit only slightly over 80% of electromagnetic power at the wavelength about 3 microns, however dry quartz refractive index being 1.42 as compared with that of sapphire being 1.72 renders dry quartz a better transmitter for a tip with uncoated facets with as total transmission of 76% in comparison with 70%. In another embodiment of these teachings, the laser beam is focused on the target through free-space by means of a concave mirror or a positive lens. In this embodiment a physical limiter may be attached to the tip end of the handpiece to designate the accurate position of the laser focus relative to the target.

Referring to FIG. 1, the handpiece shown in FIG. 1 is set to operate in the mode of emitting electromagnetic radiation from the DPSS laser in the second range of wavelengths, in one embodiment, in the wavelength range of 2500 nm to 3500 nm. The system shown therein comprises a cap 110 made of an undoped crystalline as the laser gain medium host material, for instance YAG, YLF, YSGG or another crystal, garnet or amorphous material suitable for hosting the laser active ions such as Er$^{+3}$. The cap is bonded, for instance, by diffusion to the thin slab 112 which is made of the host material as 110 doped with rare earth element laser active ions. The cap is shaped as a trapezoid having its tapered facets polished and coated, where coating 114 has maximum transmissivity at the pump wavelength and maximum reflectivity at the DPSS laser wavelength, and coating 116 that has maximum reflectivity at the pump wavelength, and partial reflectivity at the DPSS laser wavelength. The laser slab 112 is attached to a heat sink 118 by means of good thermal contact, such as may be achieved by metalizing the laser gain medium soldered to a good thermal conductor, for instance copper, by soft solder materials as GaAs and Indium. The pump laser beam 120, delivered by a fiber 122 is focused by lens 124 and aimed by prism 126 at the DPSS laser gain medium constituted by the thin slab 118. The pump laser beam's energy is partly absorbed on its path into the laser slab, however, the unabsorbed fraction is reflected from the slab wall due to total reflection angle relative to the incident pump beam or due to suitable coating, at an angle equal to that of the angle of incidence. That angle is normally incident on the cap facet on account of proper cap design. The residue pump is thereafter retroreflected off of facet 116 thus pumping further the gain medium of the DPSS laser. On pumping the DPSS laser begins lasing, such that its photons bounce inside an optical resonator formed by the coated facets 114 and 116. Facet 114 may be shaped as a spherical convex surface, attributing stability to the DPSS laser resonator and forming a TEM$_{00}$ laser mode 130 designed to exactly overlap with the pump focal spot which acts as a soft aperture. Likewise, facet 116 may be shaped as a spherical convex surface, attributing further stability to the DPSS laser resonator and forming a so called confocal laser cavity. This would in turn refocus the retroreflected pump onto the pumped laser medium. In any event, facet 116 is partly reflective to the wavelength of the DPSS laser, forming an outcoupling mirror. Thus the DPSS laser having a wavelength between 2500 nm and 3500 nm generated in the slab 112 generates a TEM$_{00}$ beam 130, nearly diffraction limited (that is, about 2 to about 5 times the diffraction limit), incident on prism 128 that rectifies the beam relative to the initial pump beam. Next the generated laser beam is incident on a concave mirror 132, predominantly having a paraboloidical shape, which may focus it onto an output tip 134 or directly on a target material. The heat sink 118 is equipped with a water inlet 136 and water outlet 138, for the purpose of cooling the laser slab. The heat sink 118 may be configured as a micro-channel heat exchanger for efficient heat transfer. The water outlet 138 ends with a plenum and orifice 140, spraying the water in a jet 142 on the target for the purpose of cooling the target zone and removing the ablation debris. Finally, the laser system is housed in a handpiece 144.

Figure 2:
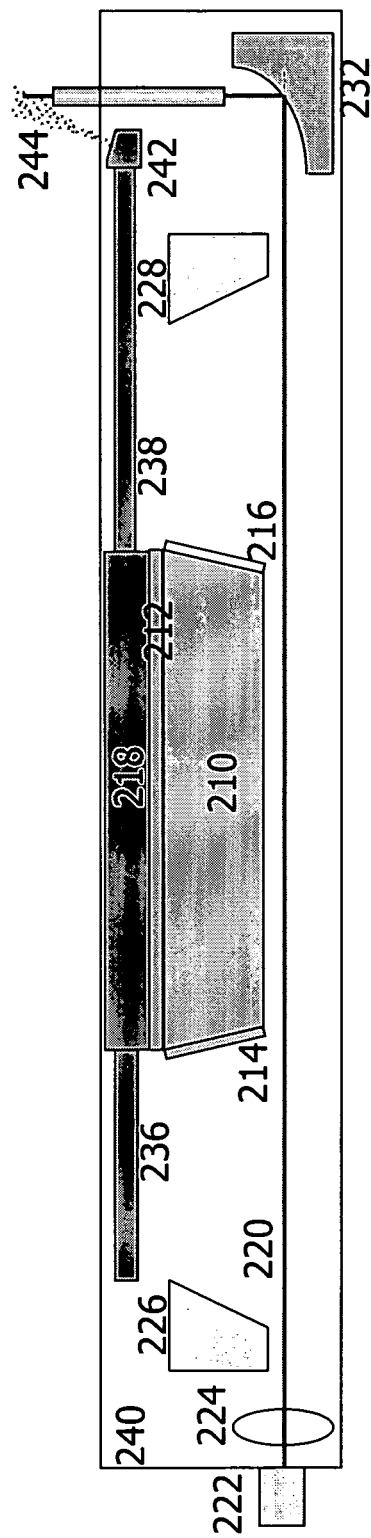
FIG. 2 is a schematic representation of another embodiment of the system of these teachings.

In order to operate in the mode of emitting the first laser in the range of 750 nm to 1600 nm, in one embodiment, a switching knob on the handpiece is set to another position, thus moving the set of prisms 126 and 128 out of the optical path of the pump laser. Shown in FIG. 2 is the mode of operation with the prisms designated as 226 and 228 out of the optical path. The pump laser beam 220 bypasses the DPSS laser medium, being relayed by the lens 224 to the output mirror 232, focused onto the tip or target thereafter. In another embodiment, the mirror 232 may be substituted by a lens coupling the beam into a tip positioned longitudinally with the laser beam. In one embodiment, the tip 234 is made of either dry quartz, in which case it may be configured as an optical fiber comprising core and cladding, or sapphire.

In the above described embodiment, the selecting component that moves the set of prisms 126 and 128 out of the optical path of the pump laser can be a mechanical component such as, but not limited to, springs and linkages configured to achieve two positions selectable by the switching knob or a solenoid having two positions selectable by the switching knob. In another instance, the selecting component can be a deflector such as, but not limited to, a galvo mirror or a A-O or E-O deflector.

Figure 3:
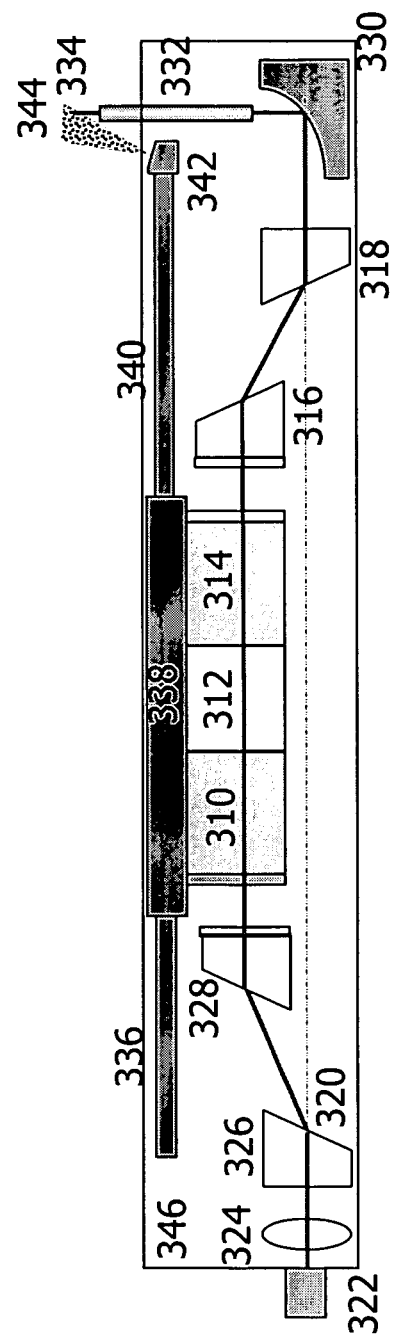
FIG. 3 is a schematic representation of yet another embodiment of the system of these teachings.

In another embodiment of these teachings, shown in FIG. 3, the DPSS laser gain medium comprises a rare earth doped crystalline host slab 312 bonded at its two facets to undoped crystalline host slabs 310 and 314. The pump laser beam 320, delivered by a fiber 322 is focused by lens 324 and directed by the prism pair 326 and 328 at the DPSS laser gain medium constituted by the slab 312. The pump laser beam 320 propagates through slab 310 virtually without being absorbed until reaching the interface with slab 312. The pump beam 320 is focused at this interface reaching maximum intensity on entering the gain medium. The propagation of the pump beam 320 through slab 312 is absorptive such as to pump the active ions to an ion state above the laser upper state, for instance $^4I_{9/2}$ for and $Er^{+3}$ ion. The pump beam residue passes over to slab 314 where again it propagates practically without being absorbed. partly absorbed on its path into the laser slab, however, its unabsorbed fraction is reflected from the slab wall due to total reflection angle relative to the incident pump beam or due to suitable coating, at an angle equal to that of the angle of incidence. That angle is substantially normally incident on the cap facet on account of proper cap design. The residue pump reaches thereafter prism 316 off which it is reflected back into the gain medium pumping it yet again. Although the normal facet of prism 316 is coated to partly reflect the DPSS laser wavelength, it is also coated for maximum reflectivity at the pump wavelength. While the normal facet of prism 328 is coated to substantially fully reflect the DPSS laser wavelength, it is also coated for maximum transmission at the pump wavelength. Thus the prisms 316 and 328 form the DPSS laser resonator. The normal facet of prism 316 has a concave surface thus stabilizing the DPSS laser and focusing the residual pump beam onto the laser gain medium. Both slabs 310 and 314 have anti-reflective coating on their outer facets for both the pump and DPSS laser wavelengths. The prism pair 316 and 318 direct the generated DPSS laser beam onto a concave mirror 330 which redirects and focuses the beam coupling it to a tip 332 from which it emerges as 334. Cooling water is conducted through a tubing 336 to a heat exchanger acting as a heat sink 338. A fraction of the cooling water is flown through tubing 340 to orifice 324 that sprinkles a water jet 344 to cool the target and wash the ablation debris off. All these components are enclosed in the handpiece 346.

Figure 4:
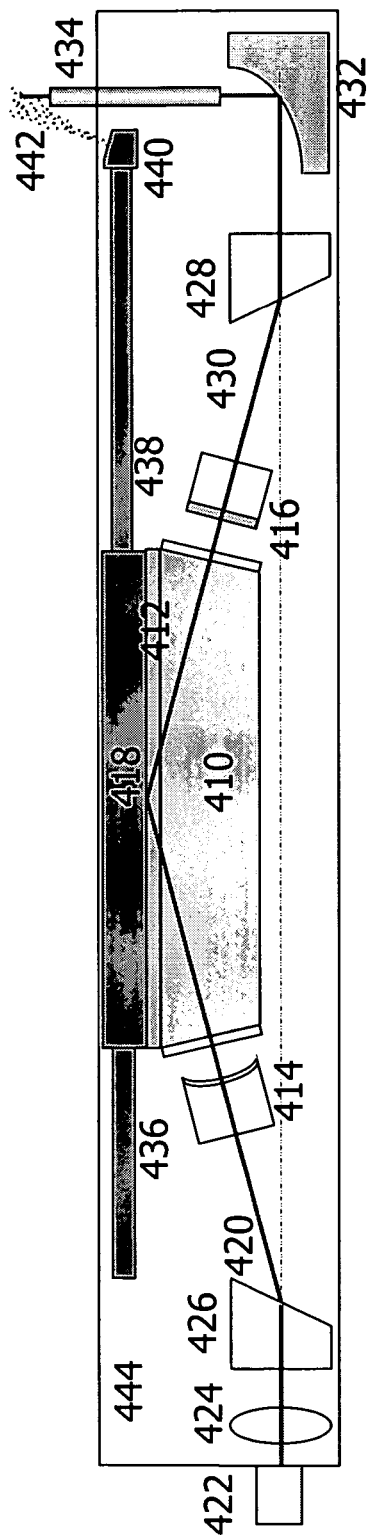
FIG. 4 is a schematic representation of still another embodiment of the system of these teachings.

Somewhat similar to FIG. 1 another embodiment of the invention is shown in FIG. 4, where at least one of the DPSS-laser optical components instead of a coating on the cap is a separate optical component. Thus, the optical component 414 is a partial mirror transmissive at the wavelength of the pump and fully reflective at the wavelength of the DPSS laser, and the optical component 416, if a separate optical component, it may be a mirror reflective at the wavelength of the pump and partially reflective at the wavelength of the DPSS laser for which it acts as an outcoupling mirror. In this configuration the cap 410 may have at least one or both facets polished and coated with anti-reflective coating for both the wavelengths of the pump and the DPSS laser. One or each of the optical components 414 and 416 may have a spherical concave surface to enhance the mode stability of the DPSS laser.

Figure 5:
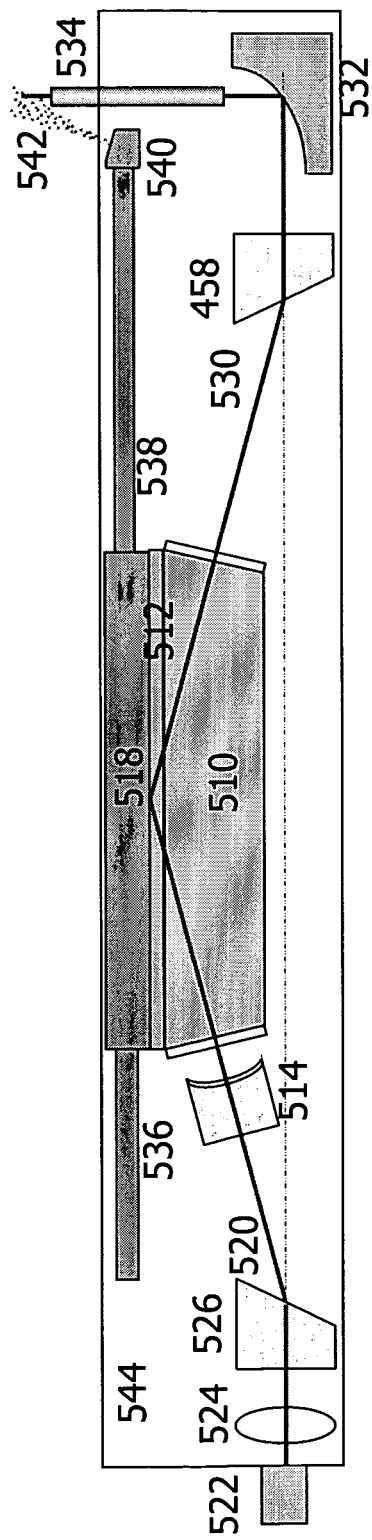
FIG. 5 is a schematic representation of a further embodiment of the system of these teachings.

Similar to FIG. 4 another embodiment of the invention is shown in FIG. 5, where one of the DPSS-laser optical components, the outcoupling laser mirror, is manifested by a partly reflective coating applied to the cap facet. Thus the optical component 514 is a partial mirror transmissive at the wavelength of the pump and fully reflective at the wavelength of the DPSS laser. In this configuration, the cap 510 may have one facet polished and coated with anti-reflective coating for both the wavelengths of the pump and the DPSS laser. The optical component 514 may have a spherical concave surface to enhance the mode stability of the DPSS laser.

Figure 6:
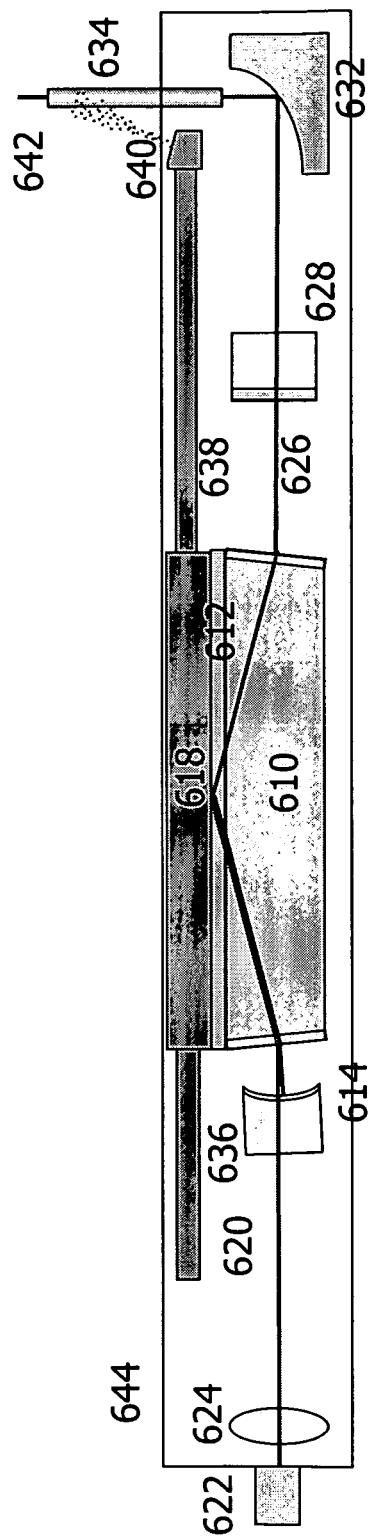
FIG. 6 is a schematic representation of yet a further embodiment of the system of these teachings

FIG. 6 shows another embodiment of the invention where the angles of the cap end-facets are cut at a greater angle than the complementary angle of the incident pump beam. Thus the pump beam 620 is focused by lens 624 and passing element 614 is incident on the facet of the crystal cap 610. Because of the incidence at an angle the pump beam is deviated, subsequently propagating into the slab 612 of whose far wall it bounces back into the cap crystal. Once absorbed in the slab 612 it generates the laser beam 626 that resonates between mirrors 614 and 628. Both slabs 610 facets have anti-reflective coatings for both the pump and DPSS laser wavelengths. Cooling water is conducted through a tubing 636 to a heat exchanger acting as a heat sink 638. A fraction of the cooling water is flown through tubing 640 to orifice 634 that sprinkles a water jet to cool the target and wash the ablation debris off. All these components are enclosed in the handpiece 644.

Figure 7:
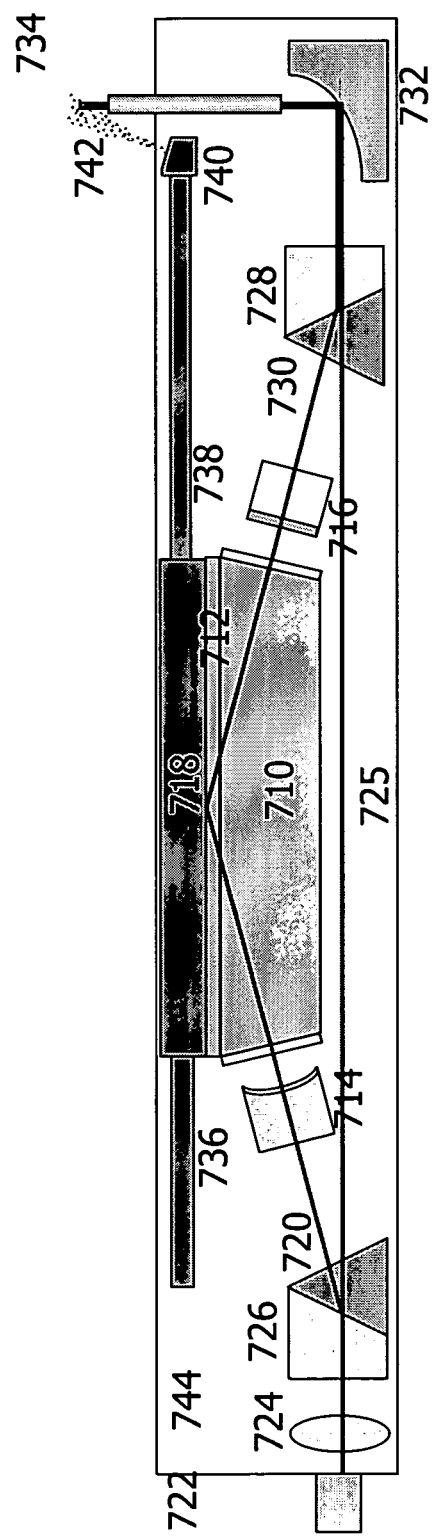
FIG. 7 is a schematic representation of still a further embodiment of the system of these teachings.

FIG. 7 shows another embodiment of the invention where instead of displacing the directing prisms out of the path of the pump beam as shown in FIG. 2, these prisms are replaced by polarizers 726 and 728 of the Thompson type which split the pump beam 720 such that the ordinary component continues in its path 725 and the extraordinary component is directed to the DPSS laser gain medium 712. At least one of the DPSS-laser resonator mirrors is constituted by a separate optical component instead of being realized as a coating on the cap. Thus the optical component 714 is a partial mirror transmissive at the wavelength of the pump and fully reflective at the wavelength of the DPSS laser, and the optical component 716, if a separate optical component, may be a mirror fully reflective at the wavelength of the pump and partly reflective at the wavelength of the DPSS laser for which it acts as an outcoupling mirror. In this configuration the cap 710 may have at least one or both facets polished and coated with anti-reflective coating for both the wavelengths of the pump and the DPSS laser. One or each of the optics 714 and 716 may have a concave surface to enhance the mode stability of the DPSS laser.

It should be noted that the above described embodiment, shown in FIG. 7, in the instance in which the pump beam comprises two ranges of wavelengths, can be utilized to allow propagation of one range of wavelengths as an output beam while allowing another range of wavelengths to be directed to pump the DPSS laser or to a beam dump. In one instance, one beam is preconditioned to be polarized so that the beam comprises only the ordinary polarization component (for example, using a polarization converter) while the other beam is conditioned to be polarized in the extraordinary polarization. The embodiment shown in FIG. 7 can also be used to select the mode of operation by utilizing a selecting component to move in or out of the path of the pump beam a polarization converter that preconditions the pump beam to be polarized so that the beam comprises only the ordinary or extraordinary polarization component.

Figure 8:
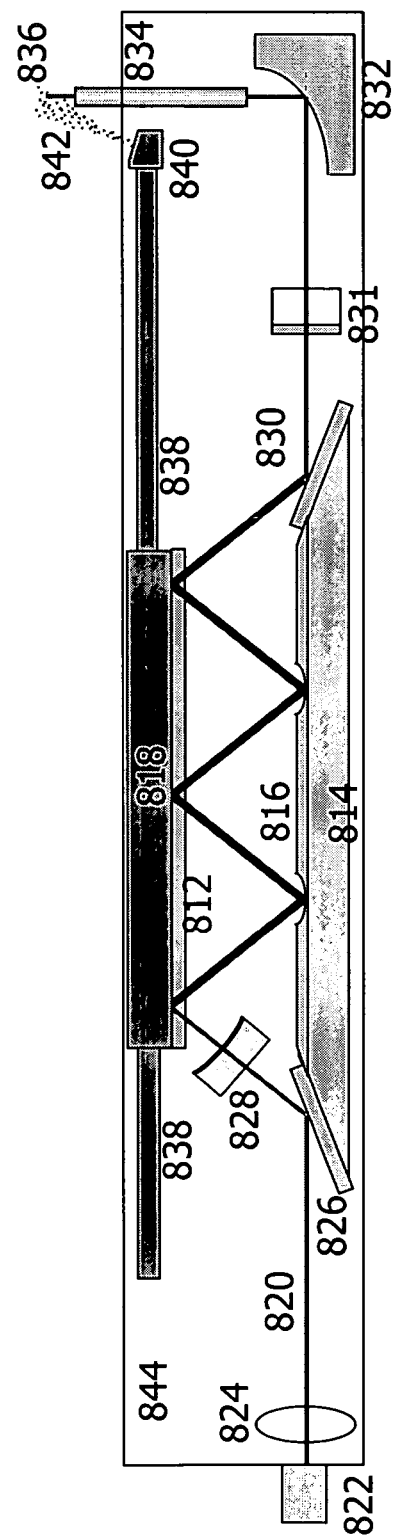
FIG. 8 is a schematic representation of another further embodiment of the system of these teachings.

Another embodiment of the invention in which the pump propagates through the DPSS laser gain medium in a zigzag path is shown in FIG. 8. Referring to FIG. 8, the DPSS laser gain medium comprises a rare earth doped crystalline host thin slab 812 in good thermal contact with a heat sink 818. The pump laser beam 820, delivered by a fiber 822 is focused by lens 824 and directed by a mirror 826 to the slab 812. It propagates through optical component 828 nearly being unaffected, where optical component 828 constitutes the fully reflective mirror of the DPSS laser. Mirror 828 is concave in order to stabilize the DPSS laser mode. The pump beam 820 once passing the slab 812 and undergoing partial absorption is reflected at an angle equal to the incidence angle, propagating thereafter out of the slab then through free-space to mirror 816 from which it bounces once again propagating toward the slab 812. Mirror 816 is concave such that the bouncing beam is refocused onto slab 812 being partly absorbed and reflected off it. The process repeats itself yet again forming a zigzag type of passage, where the gain medium is repeatedly pumped. The generated DPSS laser beam is made to co-propagate with the pump beam by appropriately aligning the resonator mirrors 828 and 831. Of these two mirror 831 is coated for partial reflection of the DPSS laser wavelength and fully reflecting the pump wavelength. Another optical component, mirror 830, directs both laser beams to mirror 831. The outcoupled DPSS laser beam reaches concave mirror 832 which redirects and focuses the beam coupling it to a tip 832 from which it emerges as beam 834. Cooling water is conducted through a tubing 838 to a heat exchanger acting as a heat sink 818. A fraction of the cooling water is flown through tubing 838 to orifice 840 that sprinkles a water jet 842 to cool the target and wash the ablation debris off. All these components are enclosed in the handpiece 844.

Figure 9:
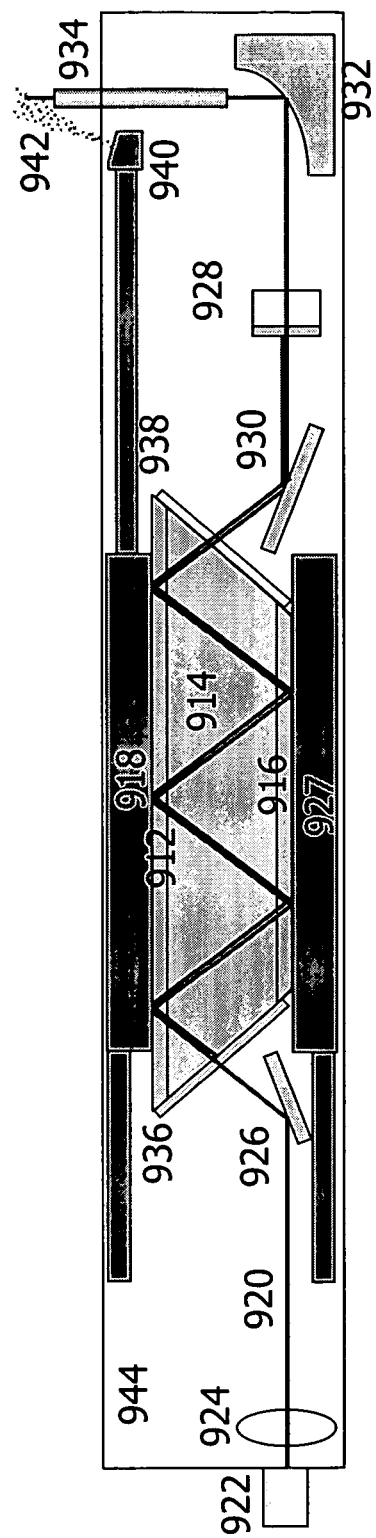
FIG. 9 is a schematic representation of yet another further embodiment of the system of these teachings.

FIG. 9 shows another embodiment of the invention in which the pump propagates through the DPSS laser gain medium in a zigzag path. Two gain medium thin slabs 912 and 916 are bonded to two parallel, long sides of an undoped host slab 914. On the other side the thin slabs are attached to two heat sinks 918 and 927 by means of good thermal contact. The pump laser beam 920, delivered by a fiber 922 is focused by lens 924 and directed by a mirror 926 to the slab 912. The pump laser beam 920 is nearly normally incident on the facet of the undoped layer 914 and propagates through the undoped layer 914 to the gain medium 912. On propagating through the slab 912 the pump beam 920 undergoes partial absorption, then is reflected at an angle equal to the incidence angle of the metal coated slab, propagating thereafter out of the doped slab then through the undoped layer 914 to the second gain medium 916 through which it propagates undergoing partial absorption bouncing again towards slab 912. The process repeats itself periodically forming a zigzag type of passage, where the gain media are repeatedly pumped. The generated DPSS laser beam is made to co-propagate with the pump beam by appropriately aligning the resonator mirror 928 relative to the coated first facet of the undoped layer, which is in turn coated as to fully reflect at the DPSS laser wavelength and to maximally transmit the pump wavelength. Another optical component, mirror 930, directs both laser beams to mirror 928. The outcoupled DPSS laser beam reaches concave mirror 932 which redirects and focuses the beam coupling it to a tip 934. Cooling water is conducted through tubes to heat sinks 918 and 927. A fraction of the cooling water is flown through tubing 938 to orifice 940 that sprinkles a water jet 942 to cool the target and wash the ablation debris off. All these components are enclosed in the handpiece 944.

Figure 10:
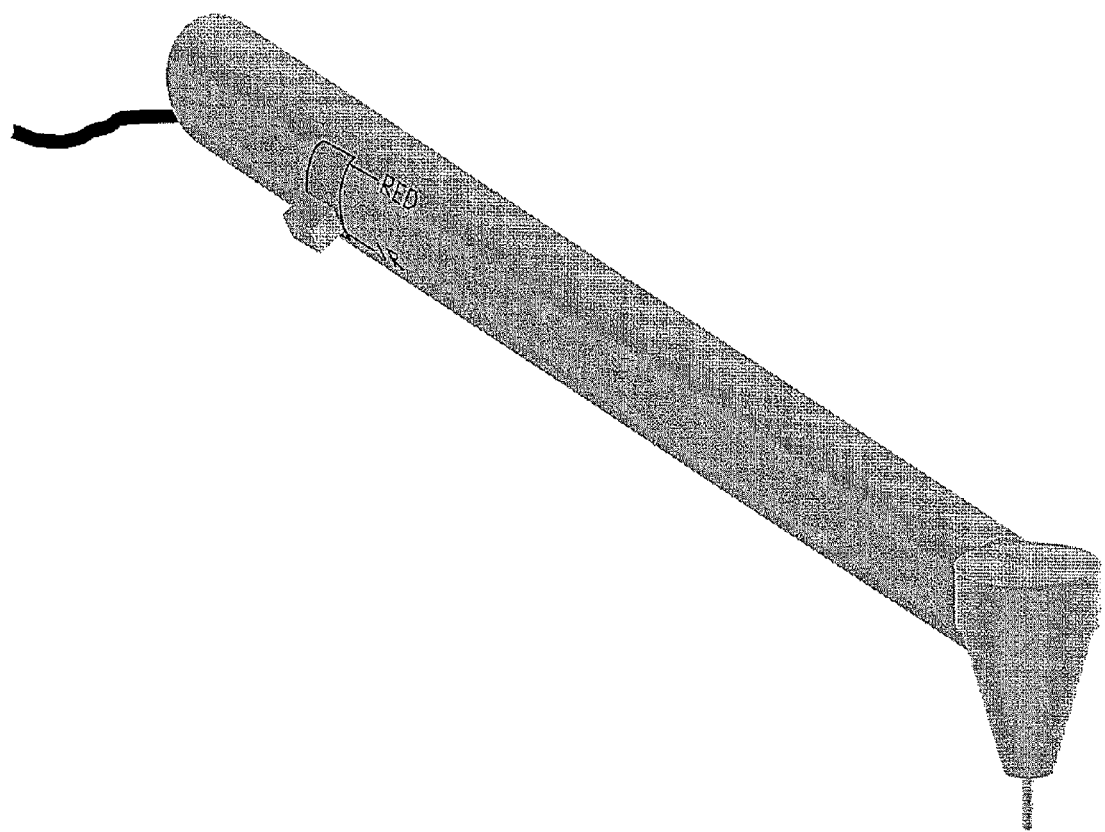
FIG. 10 is a schematic graphical representation of an exterior view of an embodiment of the system of these teachings.
Figure 11:
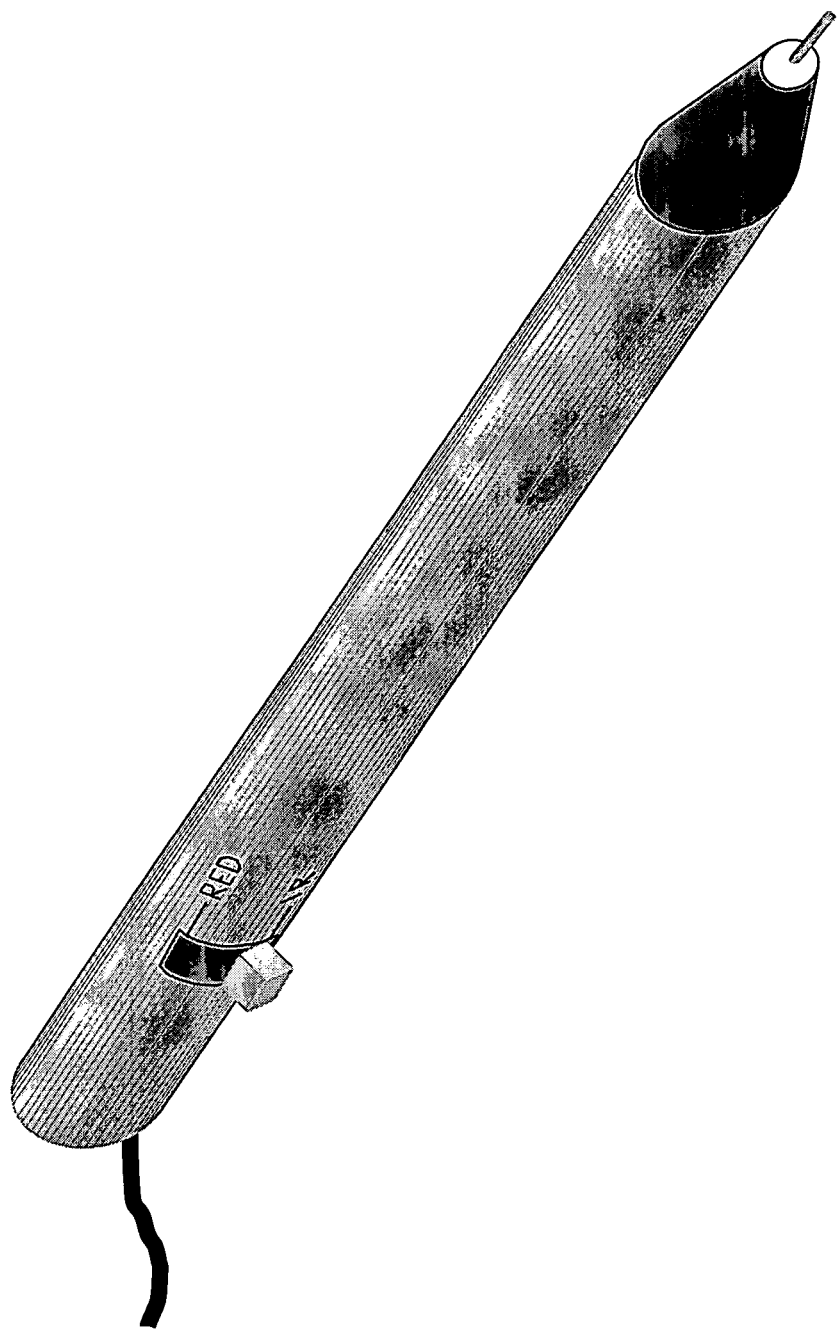
FIG. 11 is a schematic graphical representation of another exterior view of an embodiment of the system of these teachings.

FIGS. 10 and 11 show an outer view of the handpiece 1010 and 1110, with two possible end-piece configurations 1020 and 1120. In both cases a switching knob 1030 and 1130 is shown having two positions indicated as "RED" designated for the emission of the diode laser and "IR" for the emission of the DPSS laser.

In one embodiment, the laser system comprises a laser diode (or laser diode array) made of semiconductor laser bars, silica fiber and a DPSS Er laser residing in a handpiece. The laser diode emits such wavelength which coincides with Er gain medium absorption spectral lines, in the range of 750 nm-1100 nm or 1450-1600 nm or both. Upon absorption of the pump radiation and once above the loss threshold the DPSS generates a beam at the wavelength around 3 microns. In an embodiment the beam of the laser diode (or laser diode array), referred to as pump, is efficiently coupled into an optical fiber predominantly made of silica which conducts this beam to the DSPP laser. Then the pump beam is efficiently outcoupled from the fiber and directed to and focused on the gain medium of the DPSS laser. In an embodiment of these teachings, the gain medium of the DPSS laser is structured as a thin, millimeter or sub-millimeter slab that is attached to an undoped host for the purpose of optical impedance matching, simple laser cavity formation, reduction of amplified spontaneous emission and enhanced heat removal thus minimizing thermal lensing. In another embodiment the gain medium is configured as slab or rod or disk or thin slab. In yet another embodiment, the gain medium is configured as two thin slabs or disks with a layer of undoped host material between the two. Further, the laser diode acting as a pump may be incident on the gain medium of the DPSS laser at a small angle ($\leq 15°$) operated according to either end or side or zigzag pumped scheme. End pumping is known in the art as a scheme where the pump laser beam co-propagates with the DPSS laser beam in the gain medium, whereas side pumping is known in the art as a scheme where the pump laser beam propagates approximately perpendicular to the DPSS laser beam in the gain medium, finally zigzag pumping is known in the art as a scheme where the pump laser beam propagates at an angle to the DPSS laser beam alternating periodically.

In an embodiment the DPSS laser is configured inside a laser cavity comprising at least two mirrors such that one mirror is fully reflective at the wavelength of the DSPP laser and the second mirror being an outcoupling mirror is partly reflective such that, upon pumping by the pump laser, a laser beam (in one embodiment, in the range of 2500 nm to 3500) nm is generated. The DPSS laser beam as well as the pump laser beam is directed to an optical element such as a mirror which couples the beam efficiently into an exit tip made predominantly of a quartz or silica or sapphire fiber. As part of these teachings the pump may be operated in a pulsed mode, thus generating a pulse train of the DPSS laser.

By the method of current modulation, the pump laser pulses may be attributed a short period, as short as 1 ns or long periods up to milliseconds or even continuously in CW mode. (In that embodiment, the system also includes means for modulating the intensity of the pump electromagnetic radiation. In one instance, those means are electrical/electronic/software systems for current modulation. Other modulators can also be used.

Modulation means can be conveniently inserted into the handpiece. In one embodiment, the modulation means comprise passive devices. For instance, but not a limited to only this instance, a saturable absorber that opens once the optical intensity has become sufficiently high that can be made of Cr:YAG for instance, can be placed inside the laser resonator and can act a Q-switch or a mode locker. A number of other conventional means of Q-switching or mode locking can also be used.

In one embodiment, the pump laser is operated in a quasi-CW mode emitting pulses with duration of a few ten microseconds to a millisecond, thus precipitating DPSS pulses of similar duration. In another embodiment the pump pulse is short and the DPSS laser can thus be gain switched to emit pulses of similar or shorter duration. The pulse duration is limited however by the instantaneous intensity or the fluence in the fiber, defined as the ratio of the laser pulse energy and the spot area of the laser beam, which must be maintained below the damage threshold. In state-of-the-art silica fiber technology the damage threshold is considered at 40 J/cm$^2$ for pulse duration of 1 ns, scaling as the square root of the pulse duration. Consequently for pulse duration of 100 μs the damage threshold is 12 kJ/cm$^2$ determining a peak intensity of 1.2 MW/mm$^2$. This threshold also determines a peak power of 150 kW for a fiber core diameter of 400 μm, and average power of 15 kW emitted at a duty cycle of 10%, i.e. repetition frequency of 1 kHz for a 100 μs pulse. The scaling rules imply a preference to longer pulses increasing the damage threshold and to higher repetition rates proportionally lowering the pulse peak power. Whereas the pump laser may be operated at high duty cycles, for instance 20%, the DPSS Er$^{+3}$ laser can generate pulses at a repetition frequency up to 10 kHz due to upper state population buildup time.

In another embodiment of these teachings, the pump laser may be a fiber laser operating at 1030 nm to 1080 nm (Yb: fiber laser) or a fiber laser operating at about 1540 nm (Er: fiber laser). In another embodiment the DPSS laser can be Q-switched producing pulses in the range of 1 ns to a few hundred nanoseconds. In a further embodiment the DPSS laser can be mode locked producing pulses with picosecond duration of or less. The last feature can be obtained by the introduction of a passive optical shutter with high nonlinear refractive index into the second laser resonator.

In an embodiment a switching knob on the handpiece has at least two settings selecting between the emission of either the pump laser or the DPSS laser from the handpiece. On selecting the first setting the laser diode bypasses the gain medium of the DPSS laser, hence a laser beam with the wavelength in the range of 750 nm to 1600 nm is emitted from the handpiece, suitable for soft tissue operation. Then, on selecting the second setting the pump laser is directed to the gain medium of the DPSS laser pumping it efficiently, hence a laser beam with the wavelength in the range of 2500 nm to 3500 nm is emitted from the handpiece, suitable for hard tissue operation. In another preferred embodiment the knob has more than two settings, permitting the emission of at least two wavelengths simultaneously. This is enabled by the replacement of a beam folding-prism with a beam-splitter that splits the pump beam such that while one split fraction serves as to pump the DPSS laser, the other fraction is directed to the target directly. In another embodiment the pump laser comprises two types of laser diodes such that one type emits power at the wavelength of 750-1100 microns and the other emits power at the wavelength of 1450-1600 microns. The knob on the handpiece has now at least four settings such that in one setting the laser beam at the wavelength of 750-1100 microns is emitted, in the second setting the laser beam at the wavelength of 1450-1600 microns is emitted, in the third setting the laser beam at the wavelength of 2500-3500 microns is emitted, in the fourth setting a combination of any combination of two laser beams as preprogrammed in the control console is emitted. In another embodiment wavelength selection is accomplished by selecting a setting on the console. In yet another embodiment the wavelength selection is accomplished by switching handpieces.

Although the teachings has been described with respect to various embodiments, it should be realized this teachings is also capable of a wide variety of further and other embodiments within the spirit and scope of the appended claims.

What is claimed is:

1. A system comprising:
an electromagnetic radiation source configured for emitting electromagnetic radiation in at least a first range of wavelengths; said at least the first range of wavelengths being selected to enable surgical operation on soft tissue;
a handheld housing;
a first reconfigurable redirecting optical component configured for being placed into one of at least two configurations; one of said at least two configurations corresponding to allowing propagation, without redirection, of at least a portion of said electromagnetic radiation in said at least the first range of wavelengths, a direction of propagation, without redirection, of said at least a portion of said electromagnetic radiation in the first range of wavelengths constituting an output direction, said first reconfigurable redirecting optical component positioned in said housing and disposed to receive electromagnetic radiation from said source of electromagnetic radiation;
an optical resonator component comprising two reflecting end pieces, one of said two reflecting end pieces being partially reflecting;
a gain medium disposed between said two reflecting end pieces;
a heat exchanger configured for providing a heat sink for said gain medium; said heat exchanger being placed in thermal contact with said gain medium;
a cooling component in thermal contact with the heat exchanger;
another one of said at least two configurations of said first reconfigurable redirecting optical component corresponding to redirecting propagation of at least another portion of said electromagnetic radiation in said at least the first range of wavelengths; said optical resonator and said gain medium being disposed such that said gain medium receives said at least another portion of said electromagnetic radiation in said at least the first range of wavelengths after being redirected;
said gain medium, said heat exchanger and said optical resonator component being positioned in said housing;
said gain medium configured for being pumped by said at least another portion of said electromagnetic radiation in said at least the first range of wavelengths after being redirected and configured for, after being pumped, emitting electromagnetic radiation in a second range of wavelengths; said second range of wavelengths being selected to enable surgical operation on hard tissue; a pumping power of said electromagnetic radiation in said at least the first range of wavelengths being selected to enable a power of emitted electromagnetic radiation in the second range of wavelengths sufficient for surgical operation on hard tissue;

a second reconfigurable redirecting optical component configured for being placed into one of at least two configurations; one of said at least two configurations of said second reconfigurable redirecting optical component corresponding to redirecting emitted electromagnetic radiation in the second range of wavelengths, said redirecting enabling propagation of the emitted electromagnetic radiation in the second range of wavelengths substantially along the output direction; another one of said at least two configurations of said second reconfigurable redirecting optical component allowing propagation, without redirection, of said at least a portion of said electromagnetic radiation in said at least the first range of wavelengths;

said second reconfigurable redirecting optical component being positioned in said housing; and a selecting component configured for selecting a configuration of said first reconfigurable redirecting optical component and said second reconfigurable redirecting optical component;

said selecting component being positioned in said housing; at least a portion of said selecting component been accessible from an exterior surface of said housing.

2. The system of claim 1, wherein at least one of the two end pieces is partially reflecting with respect to a predetermined range of wavelengths and fully reflecting with respect to another predetermined range of wavelengths.

3. The system of claim 1, wherein the heat exchanger utilizes water to remove heat.

4. The system of claim 3, wherein said water is also used to cool a target of surgical operation and washing debris generated by an ablation process.

5. The system of claim 1, wherein the first and second reconfigurable optical components are mechanically movable in and out of the optical path.

6. The system of claim 5, wherein, when the first and second reconfigurable optical components are in the optical path, the gain medium receives the electromagnetic radiation in a first range of wavelengths and emits electromagnetic radiation in a second range of wavelengths.

7. The system of claim 6, wherein said first range of wavelengths is a range of wavelengths selected from the group consisting of 750 to 1100 nm, and 1450 to 1600 nm.

8. The system of claim 6, wherein said second range of wavelengths is a range of 2500 to 3500 nm.

9. The system of claim 6, wherein said heat exchanger is configured for cooling said gain medium to a temperature sufficient to generate the electromagnetic radiation in the second range of wavelengths at a conversion efficiency of at least 15%.

10. The system of claim 6, wherein one of the end pieces of said optical resonator component is partially reflective at the second range of wavelengths and fully reflective at the first range of wavelengths.

11. The system of claim 6, wherein one of the end pieces of said optical resonator component is fully reflective at the second range of wavelengths and fully transmissive at the first range of wavelengths.

12. The system of claim 6, wherein said emitted electromagnetic radiation in the second range of wavelengths is pulsed.

13. The system of claim 5, wherein, when the first and second reconfigurable optical components are out of the optical path, the electromagnetic radiation in a first range of wavelengths traverses from the optical input end to the optical output end, bypassing the gain medium.

14. The system of claim 1, wherein said heat exchanger comprises a micro-channel heat exchanger.

15. The system of claim 1, further comprising an electromagnetic radiation source for generating the electromagnetic radiation of at least a first range of wavelengths.

16. The system of claim 15, wherein a power of said electromagnetic radiation source is in a range of 1 W to 1 kW.

17. The system of claim 15, further comprising means for modulating an intensity of the generated electromagnetic radiation.

18. The system of claim 17, wherein said means for modulating comprises a current modulating component.

19. The system of claim 17, wherein said emitted electromagnetic radiation in at least the first range of wavelengths is pulsed.

20. The system of claim 15, further comprising an optical fiber disposed to receive electromagnetic radiation from said electromagnetic radiation source and to provide the received electromagnetic radiation to the optical input end.

21. The system of claim 15, Wherein said electromagnetic radiation source comprises at least one laser diode.

22. The system of claim 15, wherein said electromagnetic radiation source comprises at least one laser diode array.

23. The system of claim 1, wherein said gain medium comprises a rare earth ion doped solid state gain media.

24. The system of claim 1, wherein said gain medium comprises a material selected from a group consisting of Erbium doped Yttrium Aluminum Garnet (Er:YAG), Erbium doped Yttrium-Scandium-Gadolinium Garnet (Er:YSGG), Erbium doped Yttrium Lithium Fluoride (Er:YLF), Erbium doped fluorinated glass and Erbium doped amorphous host material.

25. The system of claim 1, wherein said gain medium comprises:
    a layer of host material doped with a laser active ion; and
    a volume of undoped host material, said volume comprising an upper surface, a lower surface, and two side surfaces;
    said layer of host material being disposed on one of said upper and lower surfaces.

26. The system of claim 25, wherein said gain medium further comprises:
    another layer of host material doped with the laser active ion, said another layer being disposed on another of said upper and lower surfaces.

27. The system of claim 26, wherein said electromagnetic radiation propagates in a zigzag manner between said layer of host material and said another layer of host material.

28. The system of claim 1, wherein said layer of host material reflects the electromagnetic radiation.

* * * * *